(12) United States Patent
Ivachtchenko et al.

(10) Patent No.: US 9,073,874 B2
(45) Date of Patent: *Jul. 7, 2015

(54) CYCLIC N,N'-DIARYLTHIOUREAS AND N,N'-DIARYLUREAS-ANDROGEN RECEPTOR ANTAGONISTS, ANTICANCER AGENT, METHOD FOR PREPARATION AND USE THEREOF

(76) Inventors: Alexandre Vasilievich Ivachtchenko, Encinitas, CA (US); Oleg Dmitrievich Mitkin, Moscow (RU)

(*) Notice: Subject to any disclaimer, the term of this patent is extended or adjusted under 35 U.S.C. 154(b) by 111 days.

This patent is subject to a terminal disclaimer.

(21) Appl. No.: 13/811,282

(22) PCT Filed: Jul. 1, 2011

(86) PCT No.: PCT/RU2011/000476
§ 371 (c)(1),
(2), (4) Date: Jan. 21, 2013

(87) PCT Pub. No.: WO2012/011840
PCT Pub. Date: Jan. 26, 2012

(65) Prior Publication Data
US 2013/0116269 A1  May 9, 2013

(30) Foreign Application Priority Data
Jul. 22, 2010 (RU) .................. 2010130618

(51) Int. Cl.
| | | |
|---|---|---|
| A61K 31/505 | (2006.01) |
| C07D 233/86 | (2006.01) |
| C07D 233/72 | (2006.01) |
| C07D 239/10 | (2006.01) |
| C07D 239/22 | (2006.01) |
| C07D 249/12 | (2006.01) |
| C07D 471/10 | (2006.01) |
| C07D 491/107 | (2006.01) |
| A61K 9/00 | (2006.01) |
| A61K 9/20 | (2006.01) |
| A61K 9/48 | (2006.01) |

(52) U.S. Cl.
CPC ............ *C07D 233/86* (2013.01); *C07D 233/72* (2013.01); *C07D 239/10* (2013.01); *C07D 239/22* (2013.01); *C07D 249/12* (2013.01); *C07D 471/10* (2013.01); *C07D 491/107* (2013.01); *A61K 9/0019* (2013.01); *A61K 9/2018* (2013.01); *A61K 9/2059* (2013.01); *A61K 9/2095* (2013.01); *A61K 9/4858* (2013.01)

(58) Field of Classification Search
None
See application file for complete search history.

*Primary Examiner* — Craig Ricci

(57) ABSTRACT

The invention relates to novel N,N'-disubstituted 2-thioxo-7-oxa-1,3-diaza-spiro[4.4]nonan-4-one-androgen receptor (AR) antagonists, an anticancer agent, a pharmaceutical composition, a medicament, and a method for treating prostate cancer.

4-[3-(4-Cyano-3-trifluoromethyl-phenyl)-4-oxo-2-thioxo-7-oxa-1,3-diaza-spiro[4.4]non-1-yl]-2-fluoro-benzamide of general formula 1 and enantiomer thereof

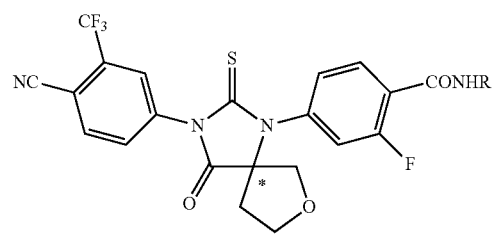

wherein:
R represents $C_1$-$C_3$alkyl.

5 Claims, 4 Drawing Sheets

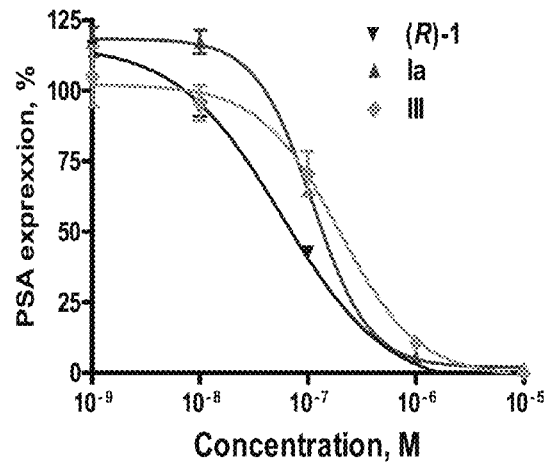
Figure 1. Inhibition of DHT-stimulated PSA expression in LnCAP cells. DHT concentration: 1 nM; $K_i$ values: 20.0±5.5nM ((R)-1), 30.8±7.7nM (Ia), 38.4 nM (III).
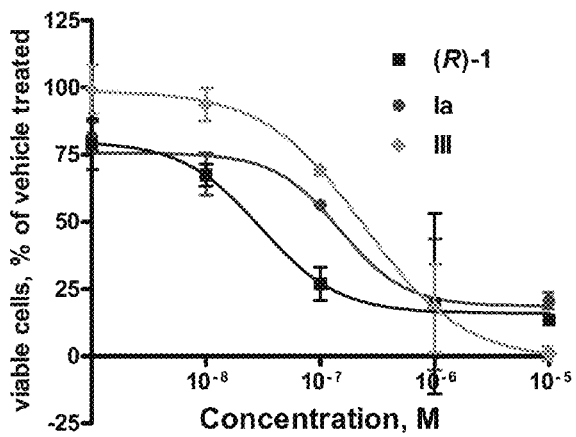
Figure 2. Inhibition of DHT-stimulated proliferation of LnCAP cells. DHT at 1nM; $IC_{50}$ values: 30 nM ((R)-1), 148 nM (Ia), 240 nM (III).

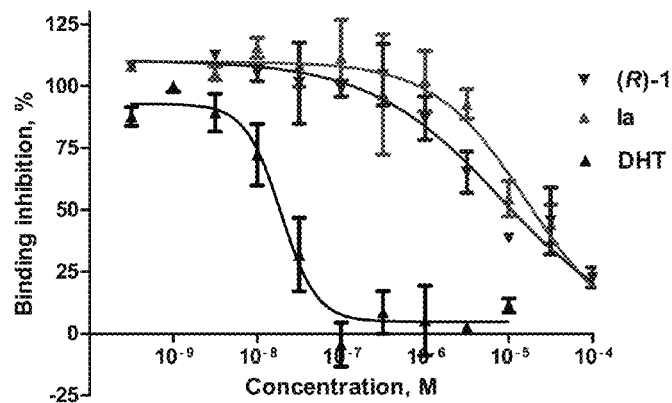
Figure 3. Competitive-binding assay vs AR ligand Fluormone™ (PolarScreen™ Androgen Receptor Competitor Assay, Invitrogen, cat.# PV4293). $IC_{50}$ values: 0.019 μM (DHT), 7.9 μM ((R)-1), 16.3 μM (Ia).
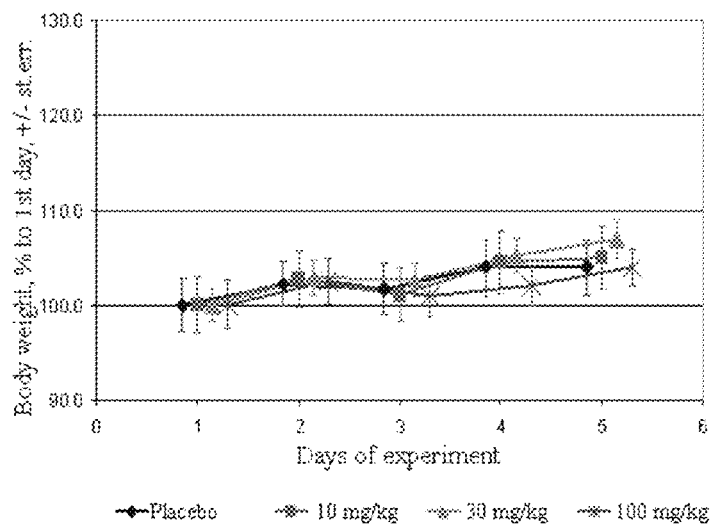
Figure 4. Weight change in male mice after peroral introduction of compound (R)-1.

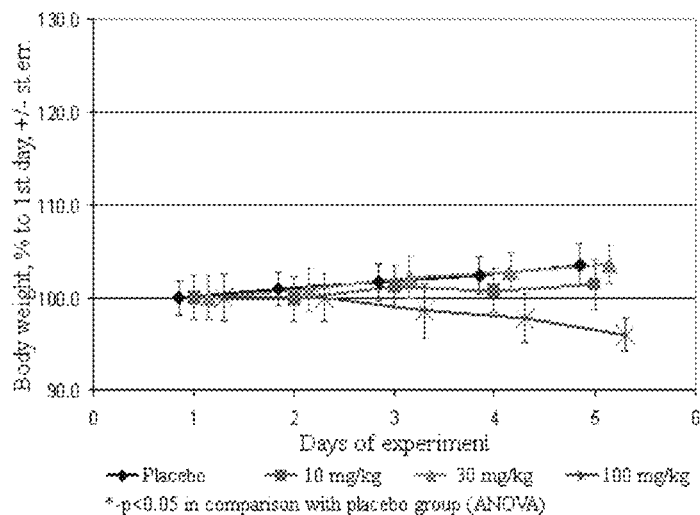
Figure 5. Weight change in male mice after peroral introduction of compound MDV3100 (Ia).
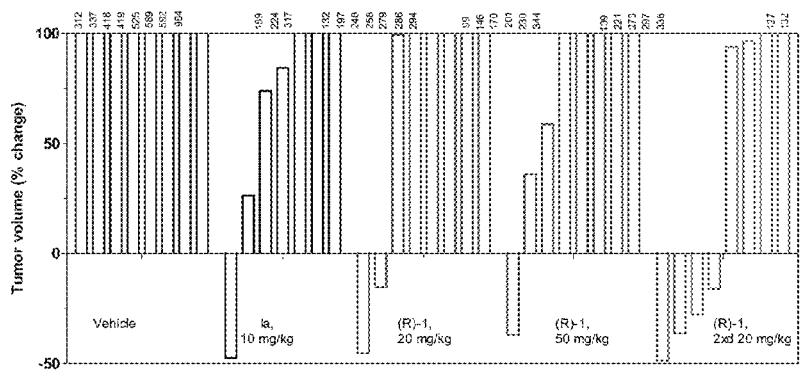
Figure 6. Antitumor activity of (*R*)-1 in a prostate cancer xenograft model.

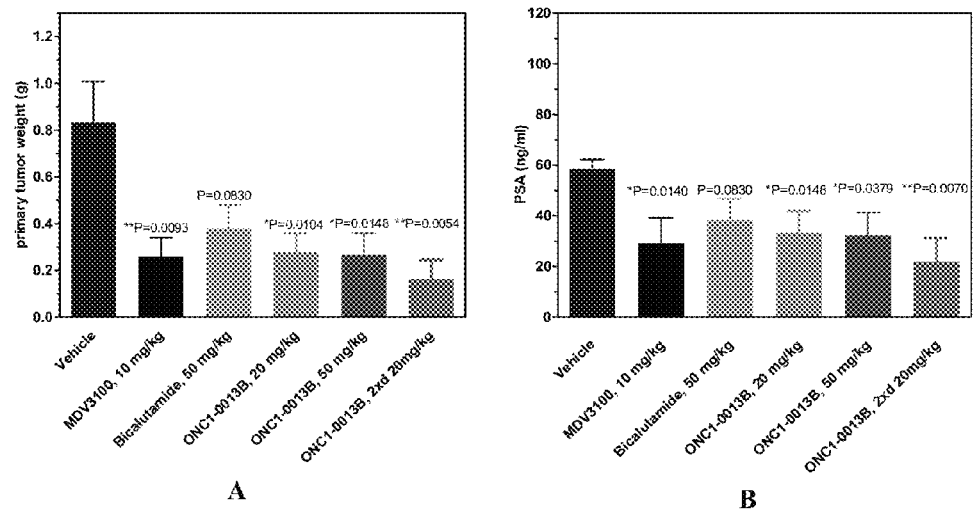
Figure 7. Antitumor activity of (R)-1 in a prostate cancer xenograft model.
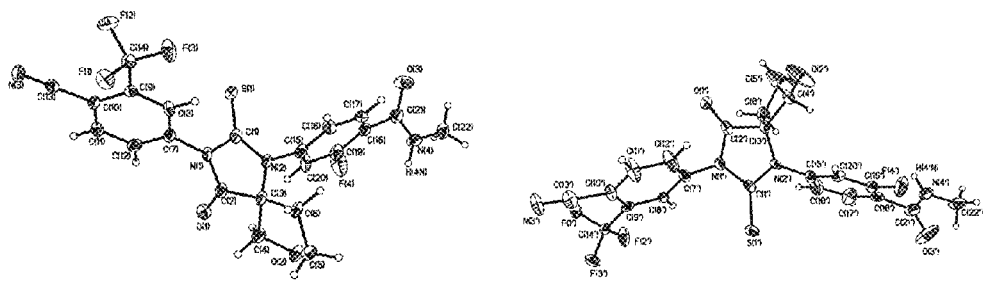
Figure 8. General view of two independent molecules in the crystal of (R)-1 in the representation of atoms as ellipsoids of thermal displacement (p = 50%).

CYCLIC N,N'-DIARYLTHIOUREAS AND N,N'-DIARYLUREAS-ANDROGEN RECEPTOR ANTAGONISTS, ANTICANCER AGENT, METHOD FOR PREPARATION AND USE THEREOF

CROSS REFERENCE TO RELATED APPLICATIONS

This application is a National stage of International Application PCT/RU2011/000476 filed Jul. 1, 2011, which claims the benefit of foreign priority to Russian Federation application RU 2010130618 of Jul. 22, 2010. The priority applications are hereby incorporated by reference in their entirety.

FIELD OF THE INVENTION

The invention relates to novel N,N'-disubstituted 2-thioxo-7-oxa-1,3-diaza-spiro[4.4]nonan-4-on-androgen receptor (AR) antagonists, an anticancer agent, a pharmaceutical composition, a medicament, and a method for treating prostate cancer.

PRIOR ART

AR antagonists 1,3-diary-5,5-dimethyl-2-thioxoimidazolidin-4-ones I-III are known to exhibit anticancer activity [WO/2006/124118; WO/2007/127010; Drug Data Rep. 2009, 31(6, 609; WO 2007126765; WO 2008119015]. In the series of 1,3-diaryl-2-thioxoimidazolidin-4-ones (I), 4-[3-[4-cyano-3 (trifluoromethyl)phenyl]-4-oxo-2-thioxoimidazolidin-1-yl]-2-fluoro-N-methylbenzamides Ia, IIa,b the highest anti-androgenic activity [M. E. Jung, S. Ouk, D. Yoo, C. L. Sawyers, C. Chen, C. Tran, J. Wongvipat. Structure-activity relationship for thiohydantoin androgen receptor antagonists for Castration Resistant Prostate Cancer (CRPC). J. Med. Chem. 2010 Apr. 8; 53 (7): 2779-2796. DOI: 10.1021/jm901488g.]

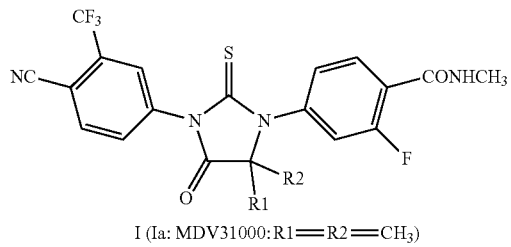

I (Ia: MDV31000: R1═R2═CH₃)

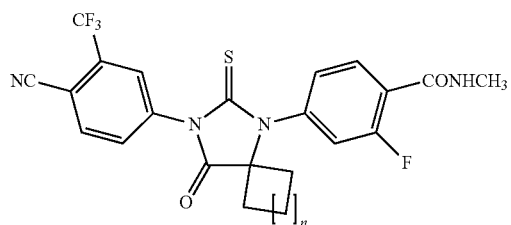

IIa (n = 1), IIb (n = 2)

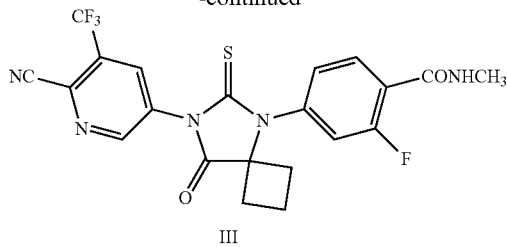

III

Transition from MDV3100 (Ia) with $IC_{50}=36$ nM [Drug Data Rep., 2009, 31(6), 609] to spiro compound II leads both to a 3.4-fold reduction in antagonistic activity and deterioration of pharmacokinetic properties. This led to the choice of MDV3100 (Ia) as the clinical candidate [Jung. J. Med. Chem. 2010 Apr. 8; 53(7): 2779-2796. doi: 0.1021/jm901488g].

Searching for highly effective anticancer medicaments exhibiting enhanced activity and reduced toxicity remains an important focus area in designing novel pharmacological remedies for cancer treatment including prostate cancer. In this context, the development of novel active anticancer agents, pharmaceutical compositions, and medicaments as well as methods for their preparation and use is of essential importance.

DISCLOSURE OF THE INVENTION

In the context of the invention, the terms are generally defined as follows:

"Active ingredient" (drugsubstance) means a physiologically active compound of synthetic or other origin (biotechnological, vegetable, animal, microbial, and so on) exhibiting pharmacological activity and being an active ingredient of a pharmaceutical composition employed in the production and preparation of medicaments.

"Alkyl" means an aliphatic hydrocarbon straight or branched chain with 1-12 carbon atoms. Branched means an alkyl chain with one or more "lower alkyl" substituents. Alkyl group may have one or more substituents of the same or different structure ("alkyl substituent") including halogen, alkenyloxy, cycloalkyl, aryl, heteroaryl, heterocyclyl, aroyl, cyano, hydroxy, alkoxy, carboxy, alkynyloxy, aralkoxy, aryloxy, aryloxycarbonyl, alkylthio, heteroarylthio, aralkylthio, arylsulfonyl, alkylsulfonylheteroaralkyloxy and so on.

"Antagonists" mean ligands that do not activate cellular responses when bound to specific receptors. Antagonists prevent agonists from binding to receptors thus blocking the transmission of a specific receptor signal.

"Hydrate" means stoichiometric or nonstoichiometric compositions of compounds or their salts with water.

"Substituent" means a chemical radical attached to a scaffold (fragment), for example, "lower alkyl substituent", "aryl substituent", "amino group substituent", "carbamoyl substituent", and "cyclic system substituent", the meanings of which are defined in this section.

"Medicament" means a compound (or mixture of compounds in the form of a pharmaceutical composition) in the form of tablets, capsules, injections, ointments, and other ready forms intended for the restoration, improvement, or modification of physiological functions in humans and animals as well as for the treatment and prophylaxis of diseases, in diagnostics, anesthesia, contraception, cosmetology, and other areas.

"Lower alkyl" means a straight or branched alkyl with 1-4 carbon atoms.

"Pharmaceutical composition" means a composition comprising an active ingredient and at least one of the components selected from a group of pharmaceutically acceptable and pharmacologically compatible fillers, solvents, diluents; auxiliary, distributing, and sensing agents; delivery agents, preservatives, stabilizers, disintegrators, moisteners, emulsifiers, suspending agents, thickeners, sweeteners, flavoring agents, aromatizing agents, antibacterial agents, fungicides, lubricants, and prolonged delivery controllers, the choice and suitable proportions of which depend on the nature and way of administration and dosage. Examples of suitable suspending agents are ethoxylated isostearyl alcohol, polyoxyethene, sorbitol and sorbitol ether, microcrystalline cellulose, aluminum metahydroxide, bentonite, agar-agar, and tragacanth as well as their mixtures. Protection against the action of microorganisms can be provided by various antibacterial and antifungal agents such asparabens, chlorobutanol, sorbic acid, and similar compounds. Said composition may also contain isotonic agents such as sugar, sodium chloride, or similar compounds. A prolonged effect of the composition can be achieved by using agents that slow down the absorption of the active ingredient, for example, aluminum monostearate or gelatin. Examples of suitable carriers, solvents, diluents, and delivery agents include water, ethanol, polyalcohols and their mixtures, natural oils (such as olive oil), and organic esters (such as ethyl oleate) for injections. Examples of fillers are lactose, milk-sugar, sodium citrate, calcium carbonate, calcium phosphate, and the like. Examples of disintegrators and distributors are starch, alginic acid and its salts, and silicates. Examples of suitable lubricants are magnesium stearate, sodium lauryl sulfate, talc, and high molecular weight polyethylene glycol. The pharmaceutical composition for peroral, sublingual, transdermal, intramuscular, intravenous, subcutaneous, local or rectal administration of active ingredient, either alone or in combination with another active compound, may be administered to humans and animals in a standard administration form, or in a mixture with traditional pharmaceutical carriers. Suitable standard administration forms include peroral forms such as tablets, gelatin capsules, pills, powders, granules, chewing-gums and peroral solutions or suspensions, sublingual and transbuccal administration forms; aerosols; implants; local, transdermal, subcutaneous, intramuscular, intravenous, intranasal, or intraocular forms, and rectal administration forms. Said pharmaceutical compositions are usually prepared using standard procedures that involve mixing an active compound with a liquid or overgrounded solid carrier.

The authors unexpectedly discovered that previously unknown 4-[3-(4-Cyano-3-trifluoromethyl-phenyl)-4-oxo-2-thioxo-7-oxa-1,3-diaza-spiro[4.4]non-1-yl]-2-fluoro-benzamide (1) are active AR antagonists

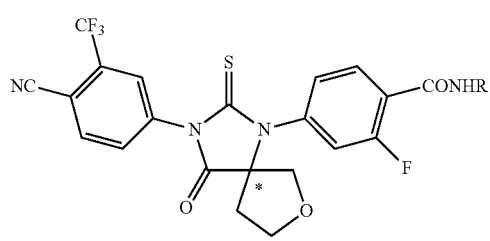

1 wherein:

R represents $C_1$-$C_3$alkyl.

For example, the activity of 4-[3-(4-cyano-3-trifluoromethyl-phenyl)-4-oxo-2-thioxo-7-oxa-1,3-diaza-spiro[4.4]non-1-yl]-2-fluoro-N-methyl-benzamide (1) is comparable with that of Ia=($K_i$ 28.2±12.5 nM), while -6-thioxo-5,7-diaza-spiro[3.4]octan-8-one (IIa) and 2-thioxo-1,3-diaza-spiro[4.4]nonan-4-one (IIb) demonstrate a lower activity. A more preferable compound is 4-[(R)-3-(4-cyano-3-trifluoromethyl-phenyl)-4-oxo-2-thioxo-7-oxa-1,3-diaza-spiro[4.4]non-1-yl]-2-fluoro-N-methyl-benzamide (R)-1 (R-stereoisomer of spiro-compound 1) having an even greater AR antagonistic activity.

Note that (R)-stereoisomer (R)-1 ($K_i$ 20 nM) is more than 10-fold more potent than (S)-stereoisomer (S)-1 ($K_i$ 215 nM).

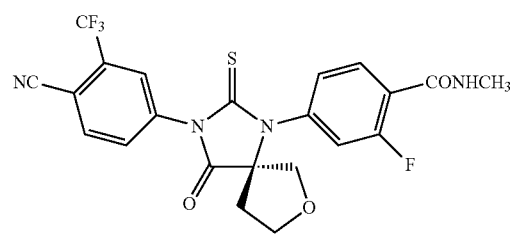

(R)-1

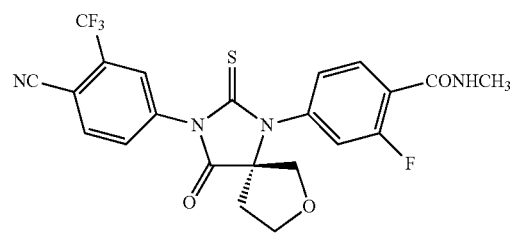

(S)-1

AR antagonist (R)-1 was identified by its ability to inhibit AR-dependent PSA expression in prostate cancer cells LnCAP. The cells were cultured in a medium containing 5% CSS for 3 days and then treated with test compounds in the presence of 5-α-dihydrotestosterone (DHT). The expression of PSA was measured in the culture medium 24 hours thereafter (FIG. 1). (R)-1 inhibits DHT-induced PSA expression ($K_i$ 20 nM) around 1.5-fold more efficiently than Ia ($K_i$ 30.8 nM) and around 1.9-fold more efficiently than III ($K_i$ 38.4 nM). The LnCAP cells were cultured for a further 5 days and the number of viable cells was then calculated. As shown in FIG. 2, (R)-1 inhibits DHT-induced cell proliferation ($IC_{50}$ 30 nM) around 6-fold more efficiently than Ia ($IC_{50}$ 184 nM) and around 8-fold more efficiently than III ($IC_{50}$ 240 nM). As shown on the FIG. 1 and FIG. 2.

Binding to rat AR ligand-binding domain was measured in competition with fluorescently labeled AR ligand Fluormone™ using a commercial assay kit and fluorescence polarization as a read-out. As shown in FIG. 3, (R)-1 binds DHT-induced cell proliferation ($IC_{50}$ 7.9 μM) around 2.1-fold more efficiently than Ia ($IC_{50}$ 16.3 μM). As shown on the FIG. 3.

New compounds 1 and (R)-1 are selective AR antagonists. For example, AR antagonist (R)-1 exhibits high selectivity on a panel of 66 targets (Table. 1).

TABLE 1

The pharmacological profile of 4-[(R)-3-(4-cyano-3-trifluoromethyl-pheny1)-4-oxo-2-thioxo-7-oxa-1,3-diaza-spiro[4.4]non-1-yl]-2-fluoro-N-methyl-benzamide (R)-1 (10 μM) in a competitive radioligand binding assay.

| # | Target | % Inhibition | # | Target | % Inhibition |
|---|---|---|---|---|---|
| 11 | A1 (h) (antagonist radioligand) | −11.8 | 41 | N neuronal α4β2 (h) (agonist radioligand) | 0.2 |
| 2 | A2A (h) (agonist radioligand) | 8.1 | 42 | opioid (non-selective) (antagonist radioligand) | 19.3 |
| 3 | A3 (h) (agonist radioligand) | −4.9 | 43 | NOP (ORL1) (h) (agonist radioligand) | −1.7 |
| 4 | α1 (non-selective (antagonist radioligand) | 0.7 | 44 | PPARγ (h) (agonist radioligand) | −19.2 |
| 5 | a2 (non-selective) (antagonist radioligand) | −3.7 | 45 | PCP (antagonist radioligand) | 0.5 |
| 6 | β1 (h) (agonist radioligand) | 1.8 | 46 | EP2 (h) (agonist radioligand) | 0.0 |
| 7 | β2 (h) (agonist radioligand) | −8.0 | 47 | IP (PGI2) (h) (agonist radioligand) | −7.3 |
| 8 | AT1 (h) (antagonist radioligand) | 0.5 | 48 | P2X (agonist radioligand) | 28.0 |
| 9 | AT2 (h) (agonist radioligand) | −6.2 | 49 | P2Y (agonist radioligand) | 33.3 |
| 10 | BZD (central) (agonist radioligand) | −16.6 | 45 | 5-HT (non-selective) (agonist radioligand) | −8.2 |
| 11 | B1 (h) (agonist radioligand) | 0.5 | 46 | sigma (non-selective) (h) (agonist radioligand) | 9.8 |
| 12 | B2 (h) (agonist radioligand) | −5.2 | 47 | GR (h) (agonist radioligand) | 29.4 |
| 13 | CB1 (h) (agonist radioligand) | −4.5 | 48 | ER (non-selective) (h) (agonist radioligand) | −7.6 |
| 14 | CB2 (h) (agonist radioligand) | 9.1 | 49 | PR (h) (agonist radioligand) | 66.6 |
| 15 | CCK1 (CCKA) (h) (agonist radioligand) | 10.6 | 50 | AR (h) (agonist radioligand) | 96.3 |
| 16 | CCK2 (CCKB) (h) (agonist radioligand) | −2.5 | 51 | TRH1 (h) (agonist radioligand) | 3.4 |
| 17 | CRF1 (h) (agonist radioligand) | −0.1 | 52 | V1 a (h) (agonist radioligand) | 12.3 |
| 18 | D1 (h) (antagonist radioligand) | −2.4 | 53 | V2 (h) (agonist radioligand) | 1.5 |
| 19 | D2S (h) (agonist radioligand) | −8.1 | 54 | Ca2+ channel (L, dihydropyridine site) (antagonist radioligand) | −2.5 |
| 20 | D3 (h) (agonist radioligand) | −4.8 | 55 | Ca2+ channel (L, diltiazem site) (benzothiazepines) (antagonist radioligand) | −23.6 |
| 21 | D4.4 (h) (antagonist radioligand) | −4.7 | | | |
| 22 | ETA (h) (agonist radioligand) | −2.5 | | | |
| 23 | ETB (h) (agonist radioligand) | −1.7 | | | |
| 24 | GABA (non-selective) (agonist radioligand) | 7.1 | 56 | Ca2+channel (L, verapamil site) (phenylalkylamine) (antagonist radioligand) | 4.0 |
| 25 | AMPA (agonist radioligand) | −23.0 | | | |
| 26 | kainate (agonist radioligand) | 13.1 | 57 | KATP channel (antagonist radioligand) | −0.8 |
| 27 | NMDA (antagonist radioligand) | 2.0 | | | |
| 28 | H1 (h) (antagonist radioligand) | 0.7 | 58 | KV channel (antagonist radioligand) | −10.1 |
| 29 | H2 (h) (antagonist radioligand) | −2.6 | | | |
| 39 | H3 (h) (agonist radioligand) | −13.0 | 59 | SKCa channel (antagonist radioligand) | −4.8 |
| 31 | I2 (antagonist radioligand) | 10.1 | 60 | Na+ channel (site 2) (antagonist radioligand) | −11.6 |
| 32 | BLT1 (LTB4) (h) (agonist radioligand) | 15.9 | | | |
| 33 | CysLT1 (LTD4) (h) (agonist radioligand) | −13.9 | 61 | Cl− channel (GABA-gated) (antagonist radioligand) | 42.4 |
| 34 | MC4 (h) (agonist radioligand) | −3.1 | 62 | norepinephrine transporter (h) (antagonist radioligand) | −1.1 |
| 35 | MT1 (ML1A) (h) (agonist radioligand) | −6.2 | 63 | dopamine transporter (h) (antagonist radioligand) | −0.3 |
| 36 | M (non0selective) (antagonist radioligand) | −8.9 | | | |
| 37 | NK1 (h) (agonist radioligand) | 14.7 | 64 | GABA transporter (antagonist radioligand) | 9.7 |
| 38 | NK2 (h) (agonist radioligand) | −8.7 | | | |
| 39 | NK3 (h) (antagonist radioligand) | −4.5 | 65 | choline transporter (CHT1) (h) (antagonist radioligand) | 9.7 |
| 40 | Y (non-selective) (agonist radioligand) | −16.4 | 66 | 5-HT transporter (h) (antagonist radioligand) | 43.5 |

New AR antagonists 1, (R)-1 are safer than their known analogs Ia and III. Thus, known AR antagonists Ia and III demonstrate significant activity (IC50~3 μM) towards GABA (non-selective) receptors, while AR antagonist (R)-1 (Table 1, Target 24) is practically inactive towards these receptors. Furthermore, the distribution of (R)-1 in the brain is less than that shown for Ia and III, which decreases the risk of GABA-related seizure development (Table 2). In addition, (R)-1 is significantly less potent in CYP3A induction than Ia and III (Table 3). Thus, ONC1-13B should be better suited for co-treatment therapy in combination with other drugs including CYP3A substrates.

TABLE 2

Distribution in the plasma and brain after single IV administration in rats (Mean ± SD, n = 3).

| Time | Drug | Plasma, ng/ml | Brain, ng/g | Brain/Plasma |
|---|---|---|---|---|
| 30 min | (R)-1, 2 mg/kg | 746 ± 104 | 145 ± 22 | 0.19 ± 0.02 |
| | Ia, 2 mg/kg | 263 ± 19 | 164 ± 19 | 0.62 ± 0.06 |
| | III, 1 mg/kg | 251 ± 29 | 241 ± 21 | 0.96 ± 0.03 |
| 120 min | (R)-1, 2 mg/kg | 522 ± 57 | 89 ± 10 | 0.17 ± 0.35 |
| | Ia, 2 mg/kg | 377 ± 153 | 152 ± 31 | 0.40 ± 0.12 |
| | III, 1 mg/kg | 153 ± 10 | 176 ± 31 | 1.15 ± 0.27 |

TABLE 3

CYP 3A induction assay.

| Drug | Concentration, μM | Positive control, % |
|------|-------------------|---------------------|
| (R)-1 | 1 | 0.0 ± 2.0 |
|       | 10 | 42.0 ± 6.1 |
| Ia | 1 | 10.0 ± 2.0 |
|    | 10 | 73.3 ± 6.8 |
| III | 1 | 16.3 ± 2.5 |
|     | 10 | 102.7 ± 13.0 |

NOTES:
% Positive control = (activity of test compounds treated cells-activity of negative control) * 100%/(activity of positive control −/activity of negative control).

Interestingly that in vivo (R)-1 is more active per unit of plasma concentration than Ia. Taking into account that in vitro (R)-1 and Ia have similar activity, this can be explained by a better distribution of (R)-1 in the tumor and by a higher free fraction of (R)-1 in the plasma. The target-distribution study revealed that the concentration of (R)-1 in the prostate is significantly higher than Ia in rats (Table 4).

TABLE 4

Distribution in the prostate after single IV administration in rats (Mean ± SD, n = 3).

| Time | Drug, Dose | Plasma, ng/ml | Prostate, ng/g | Prostate/Plasma |
|------|-----------|---------------|----------------|-----------------|
| 30 min | (R)-1, 2 mg/kg | 746 ± 104 | 1159 ± 164 | 1.55 ± 0.08 |
|        | Ia, 2 mg/kg | 263 ± 19 | 102 ± 4 | 0.39 ± 0.03 |
|        | III, 1 mg/kg | 251 ± 29 | 487 ± 73 | 1.94 ± 0.24 |
| 120 min | (R)-1, 2 mg/kg | 522 ± 57 | 625 ± 108 | 1.20 ± 0.36 |
|         | Ia, 2 mg/kg | 377 ± 153 | 124 ± 27 | 0.33 ± 0.16 |
|         | III, 1 mg/kg | 153 ± 10 | 482 ± 120 | 3.15 ± 0.94 |

Novel AR antagonist (R)-1 is more than three times less toxic than the (Ia) antagonist: its maximum tolerated dose (MTD) determined in experiments with male CD-1 mice is equal to MTD>100 mg/kg, whilst MTD for MDV3100 is about 30 mg/kg (FIGS. 4 and 5).

The above data on AR antagonist activity, selectivity, toxicity, and distribution reflect a higher therapeutic index of novel compounds in comparison with known AR antagonists.

The antitumor efficacy of (R)-1 administered once daily at 20 or 50 mg/kg is comparable with Ia administered once daily at 10 mg/kg. (R)-1 administered twice daily at 20 mg/kg shows the highest antitumor efficacy. Analysis of individual tumors revealed that Ia and (R)-1 stimulate tumor regression. In the group treated with (R)-1 twice daily, 4 of 8 tumors regressed (FIG. 6). SCID male mice bearing LnCAP-Z2 tumors (mean volume~160-190 mm$^3$) were treated daily by oral gavage with vehicle or drugs for 21 days. Individual tumor volume change by the end of the study. Percentage of change in individual tumor volumes as compared to the start of treatment.

The PSA expression directly correlates with a decrease in tumor size As shown on the FIG. 7 (compare FIGS. 7A and 7B). SCID male mice bearing LnCAP-Z2 tumors (mean volume~160-190 mm$^3$) were treated daily by oral gavage with vehicle or drugs for 21 days. Individual tumor volume change by the end of the study. Percentage of change in individual tumor volumes as compared to the start of treatment.

Together, these data show that (R)-1 is very potent in inhibiting the proliferation of prostate cancer cells in vivo. The efficacy of (R)-1 is comparable with or even higher than that of Ia.

The present invention is a novel anticancer agent that is 4-[3-(4-cyano-3-trifluoromethyl-phenyl)-4-oxo-2-thioxo-7-oxa-1,3-diaza-spiro[4.4]non-1-yl]-2-fluoro-N-methyl-benzamide (1) or 4-[(R)-3-(4-cyano-3-trifluoromethyl-phenyl)-4-oxo-2-thioxo-7-oxa-1,3-diaza-spiro[4.4]non-1-yl]-2-fluoro-N-methyl-benzamide (R)-1.

The subject of the present invention is a method for the preparation of compounds 1 and (R)-1.

Compound 1 was prepared by the interaction of 4-isothiocyanato-2-trifluoromethyl-benzonitrile (2) with 4-(3-cyano-tetrahydro-furan-3-ylamino)-2-fluoro-N-methyl-benzamide (3). Enantiomer (R)-1 was isolated from racemate 1.

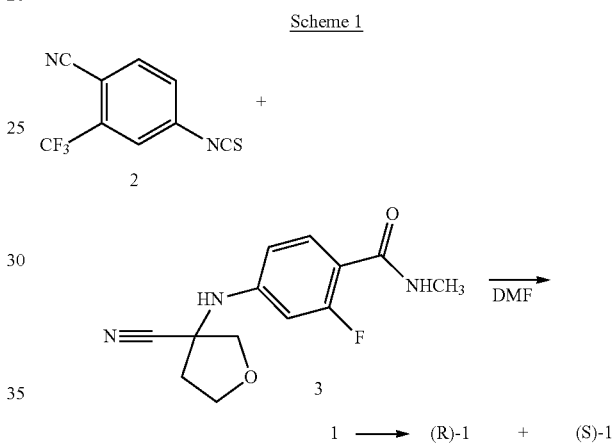

Scheme 1

Enantiomer (R)-1 was also prepared by the interaction of 4-isothiocyanato-2-trifluoromethyl-benzonitrile (2) with (R)-3-(3-fluoro-4-methylcarbamoyl-phenylamino)-tetrahydro-furan-3-carboxylic acid ((R)-4) or its methyl ester (R)-5 (Scheme 2).

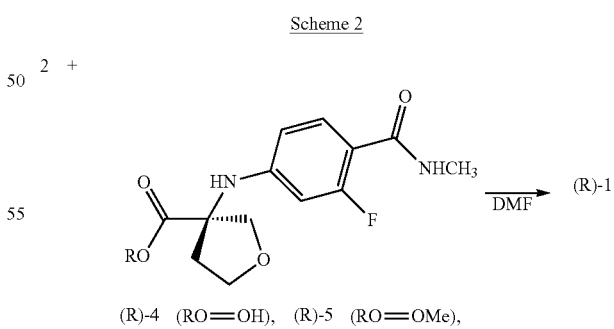

Scheme 2

The best results were obtained with enantiomer (R)-1 prepared by the interaction of isothiocyanate 2 with (R)-3-{3-fluoro-4-[hydroxy-(2-trimethylsilanyl-ethoxymethyl)-carbamoyl]-phenylamino}-tetrahydro-furan-3-carboxylic acid ((R)-6) and the resulting product (R)-7 converted into the target product (R)-1 (Scheme 3).

Scheme 3

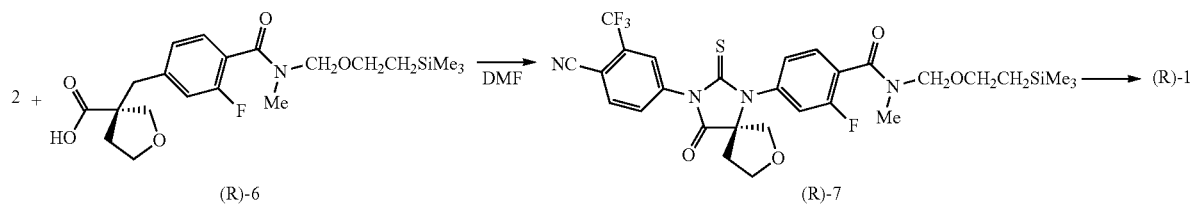

The subject of this invention relates to starting reagents of general formula 8 and enantiomers thereof.

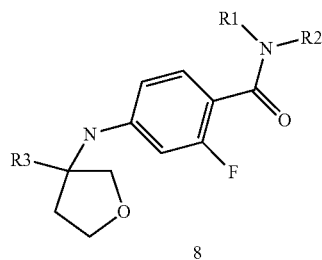

wherein:
R1 is $C_1$-$C_3$alkyl; R2 is H or $Me_3SiCH_2CH_2OCH_2$; R3 is $CO_2H$, $CO_2Me$.

The preferred starting reagents are 4-(3-cyano-tetrahydro-furan-3-ylamino)-2-fluoro-N-methyl-benzamide (3), (R)-3-(3-fluoro-4-methylcarbamoyl-phenylamino)-tetrahydro-furan-3-carboxylic acid ((R)-4), methyl (R)-3-(3-fluoro-4-methylcarbamoyl-phenylamino)-tetrahydro-furan-3-carboxylate (R)-5, and (R)-3-{3-fluoro-4-[hydroxy-(2-trimethylsilanyl-ethoxymethyl)-carbamoyl]-phenylamino}-tetrahydro-furan-3-carboxylic acid ((R)-6).

4-(3-Cyano-tetrahydro-furan-3-ylamino)-2-fluoro-N-methyl-benzamide (3) was prepared by the interaction of 4-amino-2-fluoro-N-methyl-benzamide (3.1), dihydrofuran-3(2H)-one (3.2), and trimethylsilylcyanide (3.3) in the presence of ytterbium(III) triflate (Scheme 4).

Scheme 4

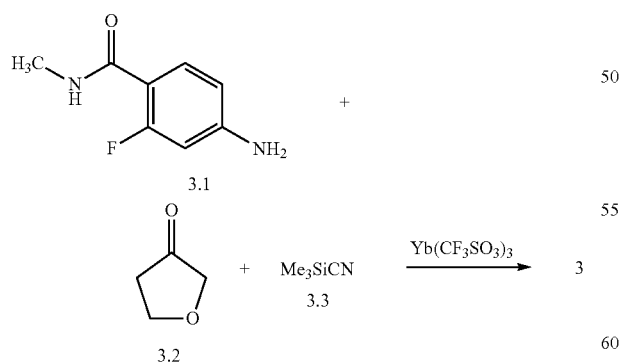

(R)-3-(3-Fluoro-4-methylcarbamoyl-phenylamino)-tetrahydro-furan-3-carboxylic acid ((R)-4) was prepared by the interaction of 2-fluoro-4-iodo-N-methyl-benzamide (4.1) with (R)-3-amino-tetrahydro-furan-3-carboxylic acid ((R)-4.2) (Scheme 5).

Scheme 5

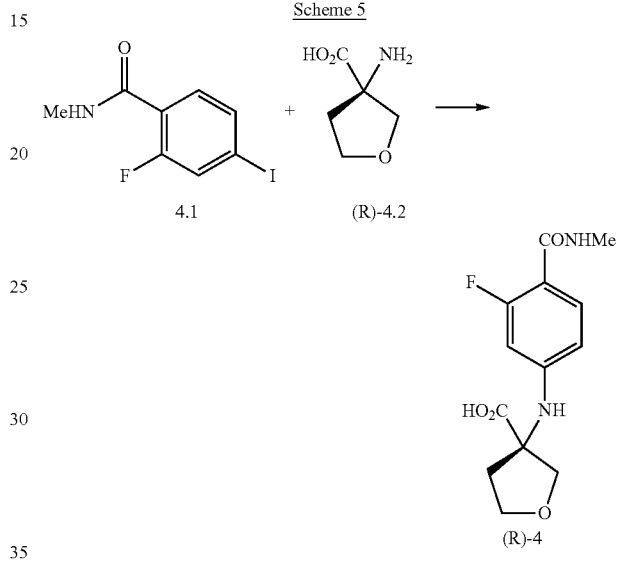

The best result was obtained when acid (R)-4 was prepared by the interaction of 4-bromo-2-fluoro-N-methyl-benzamide (4.3b) with butyl (R)-3-amino-tetrahydro-furan-3-carboxylate ((R)-4.3) with the resulting product (R)-4.5 converted into target acid (R)-4 (Scheme 6).

Scheme 6

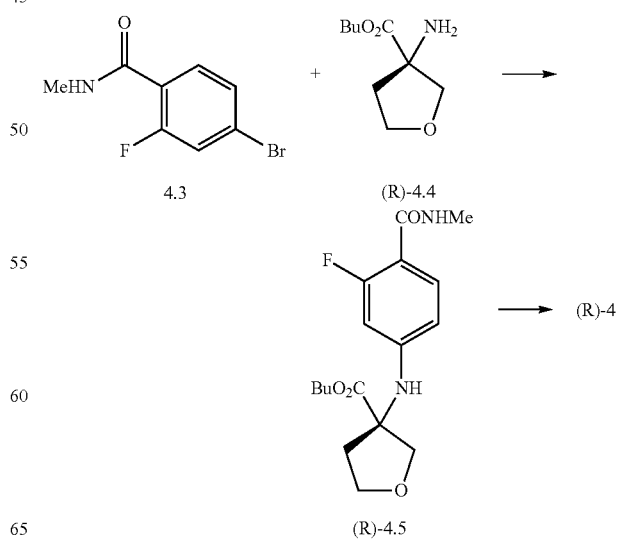

Methyl (R)-3-(3-fluoro-4-methylcarbamoyl-phenylamino)-tetrahydro-furan-3-carboxylate (R)-5 was prepared by reacting acid (R)-4 with methanol in the presence of thionyl chloride (Scheme 7).

Scheme 7

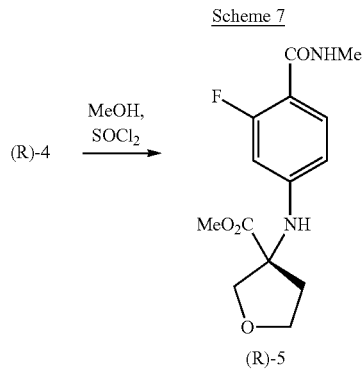

(R)-3-{3-Fluoro-4-[hydroxy-(2-trimethylsilanyl-ethoxymethyl)-carbamoyl]-phenylamino}-tetrahydro-furan-3-carboxylic acid ((R)-6) was prepared by the interaction of 2-fluoro-4-iodo-N-methyl-N-(2-trimethylsilanyl-ethoxymethyl)-benzamide (6.1) with (R)-3-amino-tetrahydro-furan-3-carboxylic acid ((R)-4.2) (Scheme 8).

Scheme 8

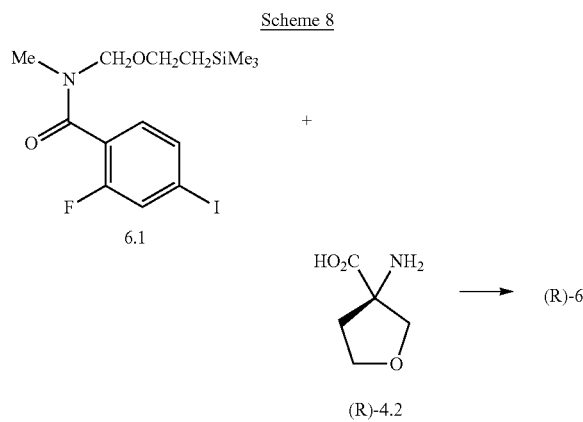

Processes for preparing the starting reagents of general formula 8 and their enantiomers including reagents (R)-4, (R)-5, and (R)-6 are also the subject of this invention. Said processes involve the interaction of compounds of general formula 9 with substituted 3-amino-tetrahydro-furan-3-ylamines of general formula 10 and their (R)-enantiomers (Scheme 9).

Scheme 9

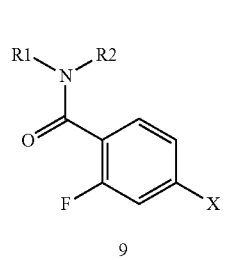

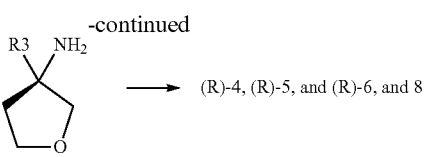

wherein:
X is Br or I; R1 is $C_1$-$C_3$alkyl; R2 is H or $Me_3SiCH_2CH_2OCH_2$; R3 is CN, $CO_2H$, $CO_2Me$.

The subject of the present invention also relates to a novel pharmaceutical composition for treating cancer, said novel composition comprising an effective amount of 4-[(3-(4-cyano-3-trifluoromethyl-phenyl)-4-oxo-2-thioxo-7-oxa-1,3-diaza-spiro[4.4]non-1-yl]-2-fluoro-N-methyl-benzamide (1) or 4-[(R)-3-(4-cyano-3-trifluoromethyl-phenyl)-4-oxo-2-thioxo-7-oxa-1,3-diaza-spiro[4.4]non-1-yl]-2-fluoro-N-methyl-benzamide (R)-1, and further comprising a pharmaceutically acceptable carrier or an excipient.

Said pharmaceutical composition may include pharmaceutically acceptable excipients. Pharmaceutically acceptable excipients mean diluents, auxiliary agents and/or carriers employed in the sphere of pharmaceutics. According to the invention, the pharmaceutical composition, in addition to 4-[3-(4-cyano-3-trifluoromethyl-phenyl)-4-oxo-2-thioxo-7-oxa-1,3-diaza-spiro[4.4]non-1-yl]-2-fluoro-N-methyl-benzamide (1) or 4-[(R)-3-(4-cyano-3-trifluoromethyl-phenyl)-4-oxo-2-thioxo-7-oxa-1,3-diaza-spiro[4.4]non-1-yl]-2-fluoro-N-methyl-benzamide (R)-1, may include other active ingredients exhibiting, among other things, anti-cancer activity, provided that they do not give rise to undesirable side effects.

According to the present invention, said pharmaceutical composition, when used in clinical practice, can be mixed up with various traditional pharmaceutical carriers.

According to the present invention, the carriers used in said pharmaceutical compositions are ones applied in the sphere of pharmaceutics for the preparation of commonly used forms and include binding agents, greasing agents, disintegrators, solvents, diluents, stabilizers, suspending agents, colorless agents, and taste flavors used for peroral forms; antiseptic agents, solubilizers, and stabilizers used in the forms for injections; and base materials, diluents, greasing agents, and antiseptic agents used in local forms.

The purpose of the present invention is also a method for the preparation of pharmaceutical compositions.

The object in view is achieved by mixing the novel anti-cancer agent with an inert excipient and/or a solvent suitable for use in combination with 4-[3-(4-cyano-3-trifluoromethyl-phenyl)-4-oxo-2-thioxo-7-oxa-1,3-diaza-spiro[4.4]non-1-yl]-2-fluoro-N-methyl-benzamide (1) or 4-[(R)-3-(4-cyano-3-trifluoromethyl-phenyl)-4-oxo-2-thioxo-7-oxa-1,3-diaza-spiro[4.4]non-1-yl]-2-fluoro-N-methyl-benzamide (R)-1

In some embodiments of the present invention, the pharmaceutical composition intended for cancer treatment, is in the form of a tablet, a capsule, or an injection placed in a pharmaceutically acceptable package.

The subject of the present invention is also a method for treating cancer comprising administering an effective dose of a pharmaceutical composition according to the instant invention to a subject in need thereof.

Medicaments can be administered perorally or parenterally, for example, intravenously, subcutaneously, intraperitoneally, locally, or intrarectally. The clinical dosage of the active ingredient (substance), pharmaceutical composition, or combination product comprising a pharmaceutically effective amount of the active ingredient can be corrected depending on the therapeutic efficiency and bioavailability of the active ingredients in the patient's body, their rate of exchange, and the washout period as well as depending on the age, sex and the severity of the patient's symptoms; the daily dosage for adults generally ranges from about 10 to about 500 mg of active ingredient, preferably from about 50 to about 300 mg. Therefore, each dosage unit prepared according to the present invention should contain from about 10 to about 500 mg of compounds 1 or (R)-1, preferably 50 to 300 mg. Depending on a doctor or pharmacist's recommendation, the above dosage can be taken several times at certain time intervals (preferably, from one to six times).

BEST EMBODIMENT OF THE INVENTION

The invention is illustrated by the following figures.

FIG. 1. Inhibition of DHT-stimulated PSA expression in LnCAP cells. DHT concentration: 1 nM; $K_i$ values: 20.0±5.5 nM ((R)-1), 30.8±7.7 nM (Ia), 38.4 nM (III).

FIG. 2. Inhibition of DHT-stimulated proliferation of LnCAP cells. DHT concentration: 1 nM; $IC_{50}$ values: 30 nM ((R)-1), 148 nM (Ia), 240 nM (III).

FIG. 3. Competitive-binding assay vs AR ligand Fluormone™ (PolarScreen™ Androgen Receptor Competitor Assay, Invitrogen, cat. #PV4293). $IC_{50}$ values: 0.019 μM (DHT), 7.9 μM ((R)-1), 16.3 μM (Ia).

FIG. 4. Weight change in male mice after peroral introduction of compound (R)-1.

FIG. 5. Weight change in male mice after peroral introduction of compound MDV3100 (Ia).

FIG. 6. Antitumor activity of (R)-1 in a prostate cancer xenograft model. SCID male mice bearing LnCAP-Z2 tumors (mean volume~160-190 mm³) treated daily by oral gavage with vehicle or drugs for 21 days. Individual tumor volume change by the end of the study. Percentage of change in individual tumor volumes compared to the start of treatment.

FIG. 7. Antitumor activity of (R)-1 in a prostate cancer xenograft model. SCID male mice bearing LnCAP-Z2 tumors (mean volume~160-190 mm³) treated daily by oral gavage with vehicle or drugs for 21 days. (A)—Tumor weight by the end of the study. Mean±SEM are presented. Unpaired t-test: vehicle vs Ia, P=0.0093, vs (R)-1 20 mg/kg, P=0.0104, 50 mg/kg, P=0.0148, 20 mg/kg twice a day, P=0.0054. (B)—PSA expression by the end of the study. Plasma samples were collected 24 hours after the last drug administration. Mean±SEM are presented. Unpaired t-test: vehicle vs Ia, P=0.0140, vs (R)-1 20 mg/kg, P=0.0148, 50 mg/kg, P=0.0379, 20 mg/kg twice a day, P=0.0070.

FIG. 8. General view of two independent molecules in the crystal of (R)-1 in the representation of atoms as ellipsoids of thermal displacement (p=50%).

The examples given below describe synthesis of new AR antagonists 1 and (R)-1 and data on their biological investigation, which illustrate but not limit the scope of the invention.

Example 1

Synthesis of N-methyl-4-{4-oxo-2-thioxo-3-[3-(trifluoromethyl)-4-cyanophenyl]-7-oxa-1,3-diazaspiro[4.4]non-1-yl}-2-fluorobenzamides 1 and (R)-1 (general method)

A solution of 4-isothiocyanato-2-(trifluoromethyl)benzonitrile 3 (342 mg, 1.5 mmol) with the corresponding 4-(3-cyano-tetrahydro-furan-3-ylamino)-2-fluoro-N-methyl-benzamide (4, 5) (0.75 mmol) in DMF (3 ml) was stirred at 110° C. for 12 h in a microwave oven. The reaction mixture was dissolved in MeOH (30 ml), 1N HCl (7.5 ml) was added and the resultant mixture was boiled for 1.5 h. The solution was evaporated in vacuo, treated with water, the solid was filtered off, washed with water and dried in vacuo. The product was isolated by HPLC to give N-methyl-4-{4-oxo-2-thioxo-3-[3-(trifluoromethyl)-4-cyanophenyl]-7-oxa-1,3-diazaspiro[4.4] non-1-yl}-2-fluorobenzamides 1 or (R)-1.

AR antagonist 1 was separated into individual stereoisomers (R)-1 and (S)-1 by HPLC with chiral column Phenomenex Lux Amylose-2 (φ5 μm, 250×20 mm). The isocratic 15/85 system of MeOH/EtOH (A) and n-hexane (B) was used as a mobile phase, the flow rate was 20 mL/min. The retention times for (R)-1 and (S)-1 were 22 min and 19 min, respectively.

4-[3-(4-Cyano-3-trifluoromethyl-phenyl)-4-oxo-2-thioxo-7-oxa-1,3-diaza-spiro[4.4]non-1-yl]-2-fluoro-N-methyl-benzamide (1). MS (ESI) [M+H]⁺ 493. ¹H NMR (400 MHz, CDCl₃) δ 8.30 (t, J=8.4 Hz, 1H), 8.02 (d, J=8.4 Hz, 1H), 7.98 (d, J=1.6 Hz, 1H), 7.85 (dd, J₁=8.4 Hz, J₂=1.6 Hz, 1H), 7.34 (dd, J₁=8.4 Hz, J₂=1.6 Hz, 1H), 7.25 (dd, J₁=11.8 Hz, J₂=1.6 Hz, 1H), 6.78 (q, J=4.4 Hz, 1H), 4.43 (d, J=10.0 Hz, 1H), 4.16 (d, J=10.0 Hz, 1H), 3.96 (m, 1H), 3.75 (m, 1H), 3.09 (d, J=4.4 Hz, 3H), 2.74 (m, 1H), 2.48 (m, 1H). ESIHRMS m/z calcd for C₂₂H₁₇F₄N₄O₃S [M+H]⁺ 493.0952; found 493.0949.

4-[(R)-3-(4-cyano-3-trifluoromethyl-phenyl)-4-oxo-2-thioxo-7-oxa-1,3-diaza-spiro[4.4]non-1-yl]-2-fluoro-N-methyl-benzamide (R)-1. MS (ESI) [M+H]⁺ 493. ¹H NMR (400 MHz, CDCl₃) δ 8.30 (t, J=8.4 Hz, 1H), 8.02 (d, J=8.8 Hz, 1H), 7.97 (d, J=1.6 Hz, 1H), 7.85 (dd, J₁=8.4 Hz, J₁=1.6 Hz, 1H), 7.33 (dd, J₁=8.4 Hz, J₁=1.6 Hz, 1H), 7.24 (dd, J₁=11.6 Hz, J₁=2.4 Hz, 1H), 6.73 (m, 1H), 4.42 (d, J=10.4 Hz, 1H), 4.16 (d, J=10.4 Hz, 1H), 3.96 (m, 1H), 3.75 (m, 1H), 3.09 (d, J=4.8 Hz, 3H), 2.73 (m, 1H), 2.48 (m, 1H). ESIHRMS m/z calcd for C₂₂H₁₇F₄N₄O₃S [M+H]⁺ 493.0952; found 493.0947. A brief X-Ray (FIG. 8) description of (R)-6: monoclinic syngony, space group P2₁, a=8.4706 (17) Å, b=14.507 (3) Å, c=17.925 (3) Å, 13=92.191 (5°), V=2201.0 (8) Å³, Z=4, T=120 K, μ(MoKα)=0.214 mm⁻¹, Dcalc=1.486 g/mm³, 19657 reflections measured (2Θ≤54), 9431 independent (R$_{int}$=0.0637). Final divergence factors: R₁=0.0603 (I>2σ(I)), wR₂=0.1271 (all data).

Example 2

4-[(R)-3-(4-cyano-3-trifluoromethyl-phenyl)-4-oxo-2-thioxo-7-oxa-1,3-diaza-spiro[4.4]non-1-yl]-2-fluoro-N-methyl-benzamide ((R)-1)

A. A mixture of (R)-5 (4.44 g, 15 mmol), isothiocyanate 2 (6.85 g, 30 mmol), DMSO (1.1 mL), and ethyl acetate (5.9 mL) was stirred in a closed vessel at 85° C. for 48 h (till the disappearance of initial (R)-5 monitored by LC-MS). After the reaction was completed, the solution was cooled to rt, the solvent was removed under reduced pressure, and the product was subjected to column chromatography on silica gel (CH₂Cl₂/MeOH=60:1) providing 5.09 g (69%) of pure (R)-1.

B. A mixture of 10.7 g (26 mmol) of (R)-6 and 8.9 g (39 mmol) of 4-isothiocyanato-2-(trifluoromethyl)benzonitrile (2) dissolved pyridine (100 mL) was stirred at 80° C. for 48 h. The residue formed after cooling and rotovapping was then treated with ethyl acetate and filtered through a 2-cm layer of silica gel. The solvent was removed under reduced pressure and the desired product was crystallized from ethanol to obtain 4.85 g (30%) of 4-{(R)-3-[4-cyano-3-(trifluoromethyl)phenyl]-4-oxo-2-thioxo-7-oxa-1,3-diazaspiro[4.4]non-1-yl}-2-fluoro-N-methyl-N-[2-(trimethylsilyl)ethoxymethyl]benzamide ((R)-7 (R)-43). MS (ESI) [M+H]+ 623.

$^1$H NMR (400 MHz, CDCl$_3$) δ 8.01 (d, J=8.0 Hz, 1H), 7.98 (s, 1H), 7.85 (d, J=8.0 Hz, 1H), 7.57 (m, 1H), 7.28 (m, 1H), 7.21 (m, 1H), 5.06 (s, 0.8H), 4.63 (s, 1.2H), 4.41 (d, J=10.4 Hz, 1H), 4.16 (d, J=10.4 Hz, 1H), 3.97 (q, J=7.6 Hz, 1H), 3.78 (m, 1H), 3.66 (t, J=8.2 Hz, 0.8H), 3.66 (t, J=8.2 Hz, 1.2H), 3.20 (s, 1.8H), 2.99 (s, 0.8H), 2.72 (m, 1H), 2.47 (m, 1H), 1.01 (t, J=8.2 Hz, 0.8H), 0.83 (t, J=8.2 Hz, 1.2H), 0.06 (s, 3.6H), −0.01 (s, 5.4H). TFA (15 mL) was added to compound (R)-7 (4.8 g, 7.7 mmol) dissolved in DCM (30 mL) and the resulting mixture was then stirred for 3 h. The solvent was removed under reduced pressure and the resulting residue was subjected to column chromatography on silica gel (CHCl$_3$/MeOH=60:1) to give 2.96 g (78%) of desired product (R)-1.

Example 3

4-(3-Cyano-tetrahydro-furan-3-ylamino)-2-fluoro-N-methyl-benzamide (3)

A mixture of compound 3.1 (155 mg, 0.92 mmol), dihydrofuran-3(2H)-one (3.2) (159 mg, 1.85 mmol), trimethylsilylcyanide (3.3)(366 mg, 3.69 mmol, 0.46 mL) and ytterbium (III) triflate (29 mg, 0.046 mmol) was stirred in a closed vessel for 12 h at 80° C. After cooling the mixture was diluted with ethyl acetate, washed with cold water, dried over Na$_2$SO$_4$ and the solvent was removed under reduced pressure. Purification was performed using column chromatography on silica gel (hexane/EtOAc=1:1). Yield of 3: 140 mg (58%). MS (ESI) [M+H]+ 264. $^1$H NMR (400 MHz, DMSO-d$_6$) δ 7.81 (t, J=4.4 Hz, 1H), 7.57 (t, J=8.6 Hz, 1H), 7.27 (s, 1H), 6.61 (dd, J$_1$=8.6 Hz, J$_2$=2.0 Hz, 1H), 6.50 (dd, J$_1$=13.6 Hz, J$_2$=2.0 Hz, 1H), 4.30 (d, J=9.2 Hz, 1H), 3.94 (m, 3H), 2.75 (d, J=4.4 Hz, 3H), 2.70 (m, 1H), 2.39 (m, 1H).

Example 4

(R)-3-(3-Fluoro-4-methylcarbamoyl-phenylamino)-tetrahydro-furan-3-carboxylic acid ((R)-4)

A mixture of compound (R)-4.4 (3.29 g, 17.6 mmol), 4-bromo-2-fluoro-N-methylbenzamide 4,3 (3.40 g, 14.7 mmol, CuI (0.53 g, 2.79 mmol), K$_2$CO$_3$ (7.97 g, 58.6 mmol), and Et$_3$N (0.2 mL) dissolved in water (6 mL) and DMF (27.5 mL) was stirred for 10 min, then 2-acetylcyclohexanone (0.41 g, 2.9 mmol) was added and the stirring continued at 100° C. for 48 h. The mixture was cooled to rt, the solvent was removed under reduced pressure, and the resulting residue was then treated with water and acidified with hydrochloric acid to pH 2-3. The resulting solution was stirred for 0.5 h, the precipitate was filtered off, washed with cold water, dried in air, then washed with ether and dried again to provide 3.35 g (81%) of (R)-3-[3-fluoro-4-(methylcarbamoyl)phenylamino]-tetrahydrofuran-3-carboxylic acid ((R)-4). MS (ESI) [M+H]+ 283. $^1$H NMR (400 MHz, DMSO-d$_6$) δ 12.96 (brs, 1H), 7.65 (t, J=4.4 Hz, 1H), 7.47 (t, J=8.8 Hz, 1H), 7.11 (brs, 1H), 6.32 (dd, J$_1$=8.8 Hz, J$_1$=2.0 Hz, 1H), 6.13 (dd, J$_1$=14.4 Hz, J$_1$=2.0 Hz, 1H), 4.11 (d, J=8.8 Hz, 1H), 3.88 (m, 3H), 2.73 (d, J=4.4 Hz, 3H), 2.54 (m, 1H), 2.15 (m, 1H).

Example 5

Methyl (R)-3-(3-fluoro-4-methylcarbamoyl-phenylamino)-tetrahydro-furan-3-carboxylate (R)-5

A. Thionyl chloride (4.81 mL, 65.9 mmol) was added dropwise (appox. for 10 min) to an ice-cooled solution of acid (R)-4 (15.5 g, 54.9 mmol) in methanol (150 mL). The resulting mixture was refluxed for 4 h. The solvent was removed under reduced pressure and the residue was dissolved in chloroform (200 mL), washed with a saturated NaHCO$_3$ solution (50 mL), and brine (50 mL), dried over Na$_2$SO$_4$, then the solvent was evaporated in vacuum and the residue was treated with ether. The precipitate was filtered off, washed with ether and dried in air to afford 12.5 g (77%) of (R)-5.

B. Iodomethane (301 mg, 2.12 mmol) was added under vigorous stirring to a mixture of compound (R)-4 (500 mg, 1.77 mmol) and K$_2$CO$_3$ (293 mg, 2.12 mmol) dissolved in DMF (4 mL) at 30° C. The resulting mixture was heated up to 40° C. and stirred maintaining the predefined temperature for 1 h, then diluted with 40 mL of water, heated up to 60° C., and filtered. The filtrate was extracted with chloroform (2×50 mL), the organic phase was washed with water, dried over Na$_2$SO$_4$, and the solvent was evaporated using a vacuum pump. The resulting residue was treated with ether, filtered off, and dried to afford 372 mg (70%) of methyl (R)-3-[3-fluoro-4-(methylcarbamoyl)phenylamino]-tetrahydrofuran-3-carboxylate ((R)-5). MS (ESI) [M+H]+ 297. $^1$H NMR (400 MHz, CDCl$_3$) δ 7.94 (t, J=8.8 Hz, 1H), 6.59 (brs, 1H), 6.39 (dd, J$_1$=8.8 Hz, J$_1$=2.4 Hz, 1H), 6.20 (dd, J$_1$=14.4 Hz, J$_1$=2.4 Hz, 1H), 4.80 (brs, 1H), 4.19 (d, J=9.6 Hz, 1H), 4.06 (m, 2H), 4.00 (d, J=9.6 Hz, 1H), 3.77 (s, 3H), 3.01 (d, J=4.4 Hz, 3H), 2.70 (m, 1H), 2.29 (m, 1H).

Example 6

(R)-3-{3-Fluoro-4-[hydroxy-(2-trimethylsilanylethoxymethyl)-carbamoyl]-phenylamino}-tetrahydro-furan-3-carboxylic acid ((R)-6)

A mixture of 4-amino-2-fluoro-N-methylbenzamide (1.68 g, 10 mmol), H$_2$SO$_4$ (0.68 mL) and water (13 mL) was gently heated until all components were completely dissolved. The mixture was cooled under stirring to 0-5° C., and NaNO$_2$ (0.7 g, 10 mmol) dissolved in water (2 mL) was then added dropwise. The resulting mixture was stirred at 0-5° C. for 0.5 h and then slowly poured into a solution of KI (5 g) in cold water (20 mL). The solution was then heated up to 80° C. and stirred for 0.5 h. After cooling, it was treated with 30 mL of chloroform and filtered. The organic layer was washed with a 5% Na$_2$SO$_3$ solution, dried over Na$_2$SO$_4$, and rotovapped. Column chromatography on silica gel (hexane/EtOAc=6:1) afforded 2.33 g (83%) of 2-fluoro-4-iodo-N-methylbenzamide (4.1). MS (ESI) [M+H]+ 280. $^1$H NMR (400 MHz, DMSO-d$_6$) δ 8.25 (m, 1H), 7.73 (d, J=10.0 Hz, 1H), 7.65 (d, J=7.8 Hz, 1H), 7.37 (t, J=7.8 Hz, 1H), 2.75 (d, J=4.4 Hz, 3H). A solution of compound 4.1 (9 g, 32 mmol) in DMF (25 mL) was added to an ice-cooled suspension of NaH (1.48 g, 36.8 mmol, 60% in oil, washed with hexane) dissolved in DMF (50 mL). The resulting mixture was vigorously stirred for 0.5 h in an ice bath, then SEM-chloride (6.46 g, 39 mmol) was added and the mixture was continuously stirred overnight at the ambient temperature. After the reaction was completed, the mixture was poured into water (400 mL) and the obtained product was extracted with benzene (2×200 mL), washed with water, dried over Na$_2$SO$_4$, and then filtered through a 3-cm layer of silica gel washing with 5:1 hexane/EtOAc. The solvent was evaporated in vacuum providing 11 g (84%) of 2-fluoro-4-iodo-N-methyl-N-[2-(trimethylsilyl)ethoxymethyl]benzamide (6.1). MS (ESI) [M+H]$^+$ 520. $^1$H NMR (400 MHz, CDCl$_3$) δ 7.58 (m, 1H), 7.52 (m, 1H), 7.12 (m, 1H), 5.01 (s, 0.8H), 4.58 (s, 1.2H), 3.63 (t, J=8.2 Hz, 0.8H), 3.31 (t, J=8.2 Hz, 1.2H), 3.14 (s, 1.8H), 2.92 (d, J=0.8 Hz, 1.2H), 0.99 (t, J=8.2 Hz, 0.8H), 0.82 (t, J=8.2 Hz, 1.2H), 0.04 (s, 3.6H), −0.01 (s, 5.4H). A mixture of 6.69 g (51 mmol) of amino acid (R)-4.2 or 9.55 g of (R)-4.3, 17.4 g (42.5 mmol) of 6.1, 1.62 g (8.5 mmol) of CuI, 23.5 g (0.17 mol) of K$_2$CO$_3$, 36 mL of water, 145 mL of DMF, and 3-5 drops of Et$_3$N was stirred for 10 min, then 6.56 g (46.8 mmol) of 2-acetylcyclohexanone was added and the stirring continued at 100° C. for 24 h. After cooling, the mixture was rotovapped, the residue was treated with 200 mL of water and acidified with hydrochloric acid to pH 2-3 (~30 mL). Then, 200 ml, of ether was added, the mixture was stirred for 0.5 h, and the resulting precipitate was filtered off, washed with 50 mL of ether, and dried in vacuum to give 10.7 g (65% from acid (R)-4.2) of (R)-3-(3-fluoro-4-{methyl[2-(trimethylsilyl)ethoxymethyl]carbamoyl}phenylamino)-tetrahydrofuran-3-carboxylic acid ((R)-6) (55% from ester (R)-4.3). MS (ESI) [M+H]$^+$ 413. $^1$H NMR (400 MHz, DMSO-d$_6$) δ 12.97 (brs, 1H), 7.07 (m, 2H), 6.31 (brs, 1H), 6.17 (brs, 1H), 4.85 (brs, 0.67H), 4.60 (brs, 1.33H), 4.10 (brs, 1H), 3.87 (brs, 3H), 3.51 (brs, 0.67H), 3.24 (brs, 1.33H), 2.93 (s, 2H), 2.86 (brs, 1H), 2.56 (brs, 1H), 2.16 (brs, 1H), 0.89 (brs, 0.67H), 0.73 (brs, 1.33H), 0.03 (m, 9H).

Example 7

Determination of Antagonistic Activity of New AR Antagonists of Formula (R)-1 and their Analogs Ia and III Towards Androgen Receptors The ability of novel AR antagonists 1 and (R)-1 and their analogs Ia and III to block androgen receptors (FIGS. 1 and 2) was determined by their effectiveness to inhibit the dihydrotestosterone stimulated expression of the prostate-specific antigen (PSA) in LNCap human prostrate cancer cells derived from the American Tissue Culture Collection (ATCC, USA). These cells are sensitive towards 5-a-dihydrotestosterone (DHT) and in the presence thereof produce cancer markers (PSA). The cells were cultured in RPMI 1640 medium (Invitrogen, USA) containing 10% calf serum (Hyclone, USA), 1% antibacterial/antifungal mixture (Sigma, USA), and 4.5% glucose. Before the experiment, the cells were washed and suspended in the same medium, in which, however, a serum treated with charcoal for removal of hormone traces was used instead of calf serum. The cells (10 000 in total) were embedded into the wells of 96-well plates at 100 µl per well and left for 4 days in an incubator at 37° C. (100% humidity) in an atmosphere of 95% air/5% CO$_2$. After incubation, AR antagonists were added to the cells in various concentrations, and then 20 nM DHT (concentration corresponding to 80-90% of maximum stimulation) was added. The cells were incubated for a further 5 days under the same conditions. Then, samples of the supracellular medium were taken and analyzed for PSA. The test was carried out according to the protocol recommended by the manufacturer of the kit for PSA measurement (Alpha Diagnostic International, USA). After wetting the wells containing PSA antibodies attached to their bottoms, 25 µl of test compounds and 100 µl of PSA antibodies pre-conjugated to horseradish peroxidase were added successively to each well. Following a 30-minute incubation at room temperature, the content of each well was removed, the wells were washed several times, and 100 µl of a peroxidase chromogenic substrate was then added to each well. The plates were held for 15 min. at room temperature and 50 µl of stop solution was then added to every well to form a dye. The absorption intensity of the dye was measured at 450 nM and the value thereof was proportional to the PSA concentration in the sample. Based on data about the dependence of DHT-related reduction of PSA synthesis on the concentration of test compounds, dose-response curves were plotted to determine IC$_{50}$ values. Said values were used for calculating apparent inhibition constants (K$_i$) for compounds of general formula I according to Cheng-Prusoff equation. [Cheng, Y., Prusoff, W. H. "Relationship between the inhibition constant (K$_i$) and the concentration of inhibitor which causes 50 percent inhibition (IC$_{50}$) of an enzymatic reaction". *Biochem Pharmacol.* (1973) 22, 3099-3108]:

$$K_i = IC_{50}/(1+L/K_D),$$

wherein L is agonist concentration (DHT), K$_D$ is receptor activation constant numerically equal to EC$_{50}$ value determined in every experiment based on the dependence of PSA synthesis stimulation on DHT concentration.

Example 8

Determination of the Maximum Tolerated Dose of Novel AR Antagonists (R)-1 and their Analog Ia (FIGS. 4 and 5)

The maximum tolerated doses (MTD) of novel antagonists (R)-1 and their analog Ia were determined in experiments on CD1 male mice at peroral administration once a day for 5 days in doses of 10, 30, and 100 mg/kg. The compound was dissolved in sterile water with addition of Tween 80. Sterile water with Tween 80 was given to control animals (Placebo group). Animals' body weight and mortality rate were estimated. Statistical comparison of groups was carried out according to a non-parametric ANOVA test using Statistica software.

Administering compounds (R)-1 and Ia in doses below 100 mg/kg did not lead to death in mice. On the 3$^{rd}$ or 4$^{th}$ day, the body weight of mice in the group that had received 100 mg/kg of test compound was lower in comparison with that of control animals; however, no statistical significance was observed (FIG. 4). The data show that compound (R)-1 has MTD>100 mg/kg.

Administering Ia in doses of 10 and 30 mg/kg did not cause death in mice. Mice treated with test compound at 100 mg/kg began to lose their weight on the 3$^{rd}$ day. On the 5$^{th}$ day, the body weight of animals in this group statistically differed from that in the Placebo group (p=0.002, FIG. 5). One animal died. The data show that compound Ia has MTD~30 mg/kg.

Example 9

(R)-1 Efficiently Inhibits Tumor Growth in a Xenograft Model of Prostate Cancer

The antitumor efficacy of (R)-1 was tested in a xenograft model of prostate cancer (FIGS. 6 and 7). Male immunodeficient mice harboring LnCAP-Z2 tumors were treated orally for 21 days with either vehicle or (R)-1 at 20 and 50 mg/kg once daily and at 20 mg/kg twice daily. Ia was administered at 10 mg/kg once daily and Bicalutamide, at 50 mg/kg once daily. Twenty-four hours after last treatment, blood samples were collected from all animals and used for measuring PSA expression and drug concentration. In addition, the concentration of drugs and Ki67 expression were measured in tumor samples.

Example 10

Preparation of Medicaments in the Form of Tablets

Starch (1600 mg), grained lactose (1600 mg), talcum (400 mg), and 4-[(R)-3-(4-cyano-3-trifluoromethyl-phenyl)-4-oxo-2-thioxo-7-oxa-1,3-diaza-spiro[4.4]non-1-yl]-2-fluoro-N-methyl-benzamide ((R)-1) (1000 mg) were mixed together and pressed into a brick. Said brick was crushed to granules and riddled through sieves to collect 14-16 mesh granules. The obtained granules were pelletized in tablets of suitable form, each weighing 560 mg.

Example 11

Preparation of medicaments in the form of capsules. 4-[(R)-3-(4-cyano-3-trifluoromethyl-phenyl)-4-oxo-2-thioxo-7-oxa-1,3-diaza-spiro[4.4]non-1-yl]-2-fluoro-N-methyl-benzamide ((R)-1) was carefully mixed with lactose powder in a ratio of 2:1. The resulting pharmaceutical composition was packed into gelatin capsules of appropriate size, each containing 300 mg.

Example 12

Preparation of medicaments in the form of compositions for intramuscular, intraperitoneal, or hypodermic injections. 4-[(R)-3-(4-cyano-3-trifluoromethyl-phenyl)-4-oxo-2-thioxo-7-oxa-1,3-diaza-spiro[4.4]non-1-yl]-2-fluoro-N-methyl-benzamide ((R)-1) (500 mg) was dissolved in a mixture of chlorobutanole (300 mg), propylene glycol (2 ml), and water for injections (100 ml). The resulting solution was filtered and placed in 1 ml ampoules, which were sealed up and sterilized in an autoclave.

INDUSTRIAL APPLICABILITY

The present invention could be used in medicine, veterinary, biochemistry.

The invention claimed is:

1. A 4-[3-(4-Cyano-3-trifluoromethyl-phenyl)-4-oxo-2-thioxo-7-oxa-1,3-diaza-spiro[4.4]non-1-yl]-2-fluoro-benzamide compound of general formula 1

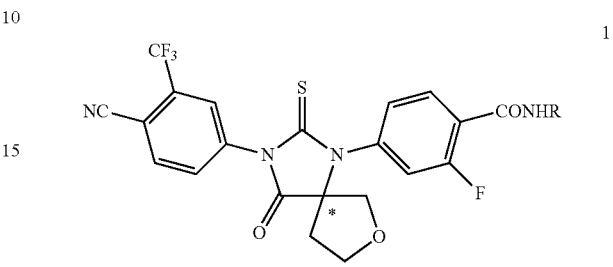

wherein:
R represents $C_1$-$C_3$ alkyl, and enantiomers thereof.

2. The compound of claim 1, wherein the compound is 4-[(R)-3-(4-Cyano-3-trifluoromethyl-phenyl)-4-oxo-2-thioxo-7-oxa-1,3-diaza-spiro[4.4]non-1-yl]-2-fluoro-N-methyl-benzamide represented by formula (R)-1

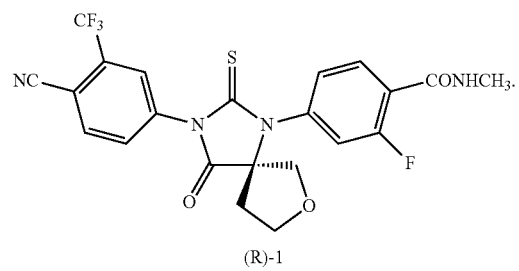

(R)-1

3. A pharmaceutical composition comprising at least one 4-[3-(4-Cyano-3-trifluoromethyl-phenyl)-4-oxo-2-thioxo-7-oxa-1,3-diaza-spiro[4.4]non-1-yl]-2-fluoro-benzamide compound of general formula 1 and enantiomers thereof.

4. The pharmaceutical composition according to claim 3 and at least one pharmaceutically acceptable carrier, inert excipient or solvent.

5. The pharmaceutical composition according to claim 4 in the form of a tablet, capsule, or injection.

* * * * *